(12) United States Patent
Demont et al.

(10) Patent No.: US 9,067,936 B2
(45) Date of Patent: Jun. 30, 2015

(54) 4-(8-METHOXY-1-((1-METHOXYPROPAN-2-YL)-2-(TETRAHYDRO-2H-PYRAN-4-YL)-1H-IMIDAZO[4,5-C]QUINOLIN-7-YL)-3,5-DIMETHYLISOXAZOLE AND ITS USE AS BROMODOMAIN INHIBITOR

(75) Inventors: Emmanuel Hubert Demont, Stevenage (GB); Katherine Louise Jones, Stevenage (GB); Robert J. Watson, Stevenage (GB)

(73) Assignee: GlaxoSmithKline LLC, Wilmington, DE (US)

( * ) Notice: Subject to any disclaimer, the term of this patent is extended or adjusted under 35 U.S.C. 154(b) by 0 days.

(21) Appl. No.: 14/237,905

(22) PCT Filed: Aug. 15, 2012

(86) PCT No.: PCT/EP2012/065918
§ 371 (c)(1),
(2), (4) Date: Feb. 10, 2014

(87) PCT Pub. No.: WO2013/024104
PCT Pub. Date: Feb. 21, 2013

(65) Prior Publication Data
US 2014/0171462 A1    Jun. 19, 2014

(30) Foreign Application Priority Data

Aug. 17, 2011  (GB) .................................. 1114103.3

(51) Int. Cl.
| | | |
|---|---|---|
| C07D 471/00 | (2006.01) | |
| A61K 31/44 | (2006.01) | |
| C07D 471/04 | (2006.01) | |
| A61K 31/4745 | (2006.01) | |

(52) U.S. Cl.
CPC .......... *C07D 471/04* (2013.01); *A61K 31/4745* (2013.01)

(58) Field of Classification Search
None
See application file for complete search history.

(56) References Cited

FOREIGN PATENT DOCUMENTS

| WO | WO 03/097641 | 11/2003 |
|---|---|---|
| WO | WO 2004/058759 | 7/2004 |
| WO | WO 2005/054237 | 6/2005 |
| WO | WO 2006/091394 | 8/2006 |
| WO | WO 2007/035935 | 3/2007 |
| WO | WO 2007/075468 | 7/2007 |
| WO | WO 2011/054843 | 5/2011 |
| WO | WO 2011/054846 | 5/2011 |
| WO | WO 2012/143416 | 10/2012 |

*Primary Examiner* — Heidi Reese
(74) *Attorney, Agent, or Firm* — Robert H. Brink

(57) ABSTRACT

Novel quinoline compounds pharmaceutical compositions containing such compounds and their use in therapy.

12 Claims, 5 Drawing Sheets

4-(8-METHOXY-1-((1-METHOXYPROPAN-2-YL)-2-(TETRAHYDRO-2H-PYRAN-4-YL)-1 H-IMIDAZO[4,5-C]QUINOLIN-7-YL)-3,5-DIMETHYLISOXAZOLE AND ITS USE AS BROMODOMAIN INHIBITOR

CROSS-REFERENCE TO RELATED APPLICATIONS

This application is filed pursuant to 35 USC 371 as a United States National Phase Application of International Patent Application Serial No. PCT/EP2012/065918 filed on Aug. 15, 2012, which claims priority from 1114103.3 filed on Aug. 17, 2011 in the United Kingdom.

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693A1 discloses a series of thienotriazolodiazepiene derivatives that are said to inhibit the binding between an acetylated histone and a bromodomain containing protein which are said to be useful as anti-cancer agents.

Patent application WO2011/054846 discloses a series of quinoline derivatives that inhibit the binding of BET family bromodomains with acetylated lysine residues.

Novel compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof

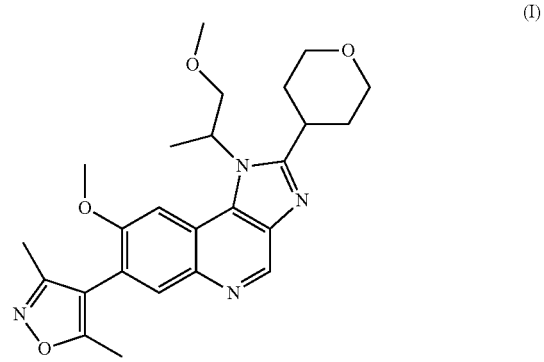 [SMILES: COCC(C)n1c(C2CCOCC2)nc2cnc3cc(-c4c(C)noc4C)c(OC)cc3c21]

(I)

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

Figure 1:
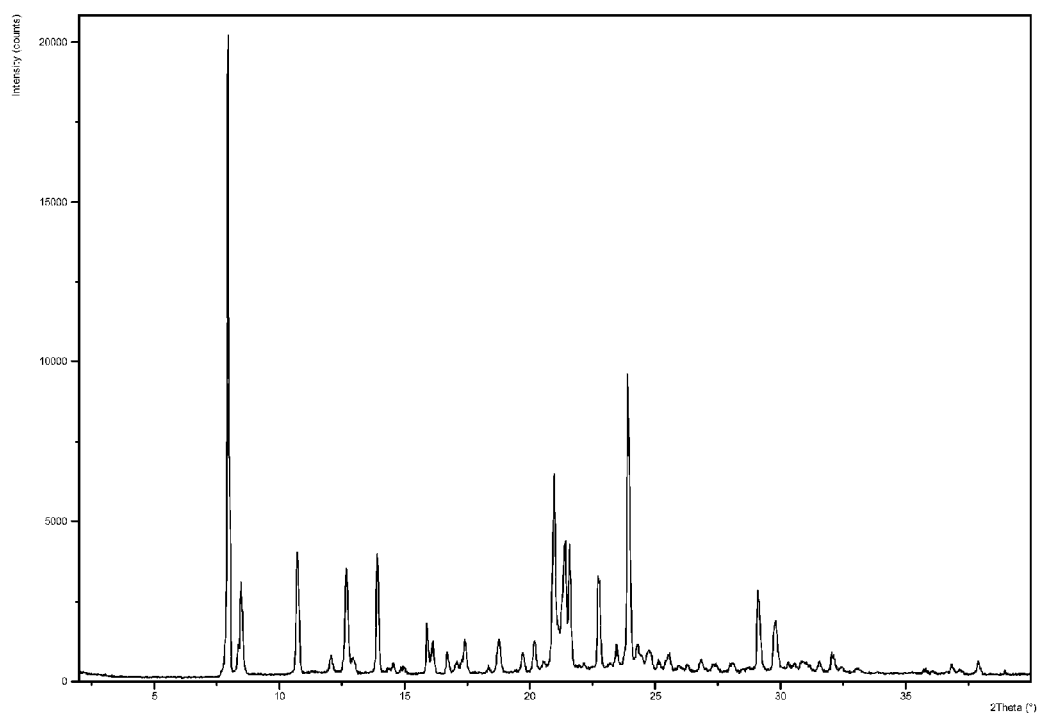
FIG. 1: Shows an XRPD pattern of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 1).

The present invention relates to a compound of formula (I) which is 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole

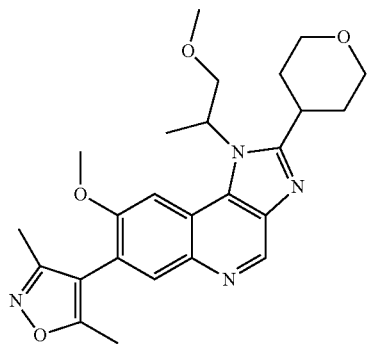

(I)

or a salt thereof.

The compound of formula (I) contains a chiral atom such that optical isomers, e.g. enantiomers may be formed. Accordingly, the present invention encompasses all isomers of the compound of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

In one embodiment there is provided a compound of formula (IA) which is 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole

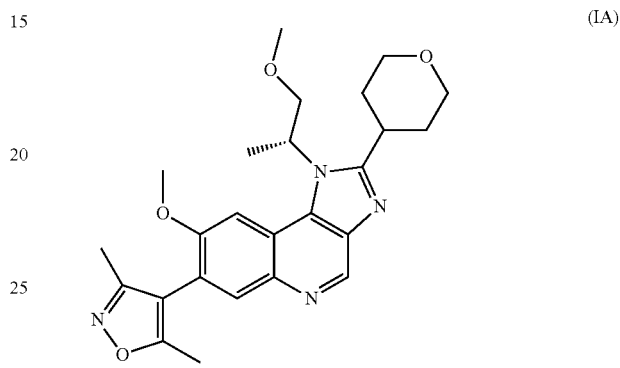

(IA)

or a salt thereof.

In a further embodiment there is provided a compound of formula (IB) which is 4-(8-methoxy-1-((S)-1-methoxypropan-2-yl)-2-(tetrahydro-2H-pyran-4-yl)-1H-imidazo[4,5-c]quinolin-7-yl)-3,5-dimethylisoxazole

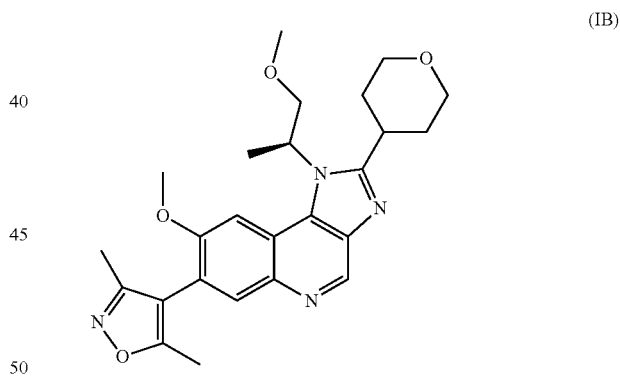

(IB)

or a salt thereof.

It will be appreciated that the compounds of formula (IA) and formula (IB) are within the scope of the compound of formula (I). As used herein, unless otherwise stated, a reference to a compound of formula (I) also includes a reference a the compound of formula (IA) and a compound of formula (IB).

It will be appreciated that the present invention covers compounds of formula (I) as the free base and as salts thereof, for example as a pharmaceutically acceptable salt thereof. In one embodiment the invention relates to compounds of formula (I) in the form of a free base. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid addition salts. For a review of suitable pharmaceutically acceptable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt. In one embodiment a pharmaceutically acceptable acid addition salt of a compound of formula (I) can comprise or be a hydrochloride, sulfate, maleate, fumarate, citrate, p-toluenesulfonate, benzenesulfonate or methanesulfonate salt. In a particular embodiment there is provided a compound of formula (IA) in the form of a hydrochloride salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of formula (I) or a pharmaceutically acceptable salt thereof, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compound of formula (IA), that is to say 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole, in the form of a free base has been found to exist in a number of different crystalline forms, namely, anhydrous forms 1, 2 and 3 and hydrated form 1. Such crystalline forms can be prepared by procedures described herein.

Thus in one embodiment, there is provided a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 1) characterised by substantially the X-ray powder diffraction (XRPD) pattern as shown in FIG. 1, wherein the XRPD pattern is expressed in terms of 2 theta angles and obtained with a diffractometer using copper Kα-radiation using procedures described herein. The XRPD pattern of anhydrous form 1 shows characteristic 2 theta angle peaks as listed in Example 9 Table 1.

Figure 2:
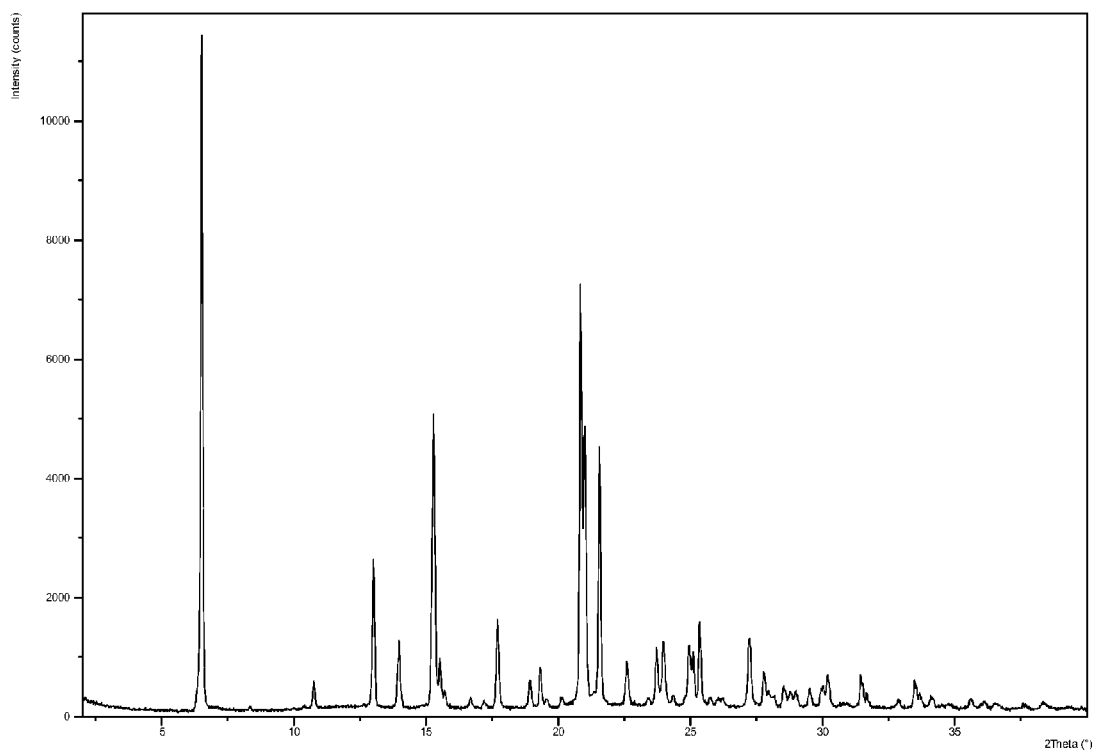
FIG. 2: Shows an XRPD pattern of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 2).

In a further embodiment, there is provided a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 2) characterised by substantially the X-ray powder diffraction (XRPD) pattern as shown in FIG. 2, wherein the XRPD pattern is expressed in terms of 2 theta angles and obtained with a diffractometer using copper Kα-radiation using procedures described. The XRPD pattern of anhydrous form 2 shows characteristic 2 theta angle peaks as listed in Example 9 Table 1.

Figure 3:
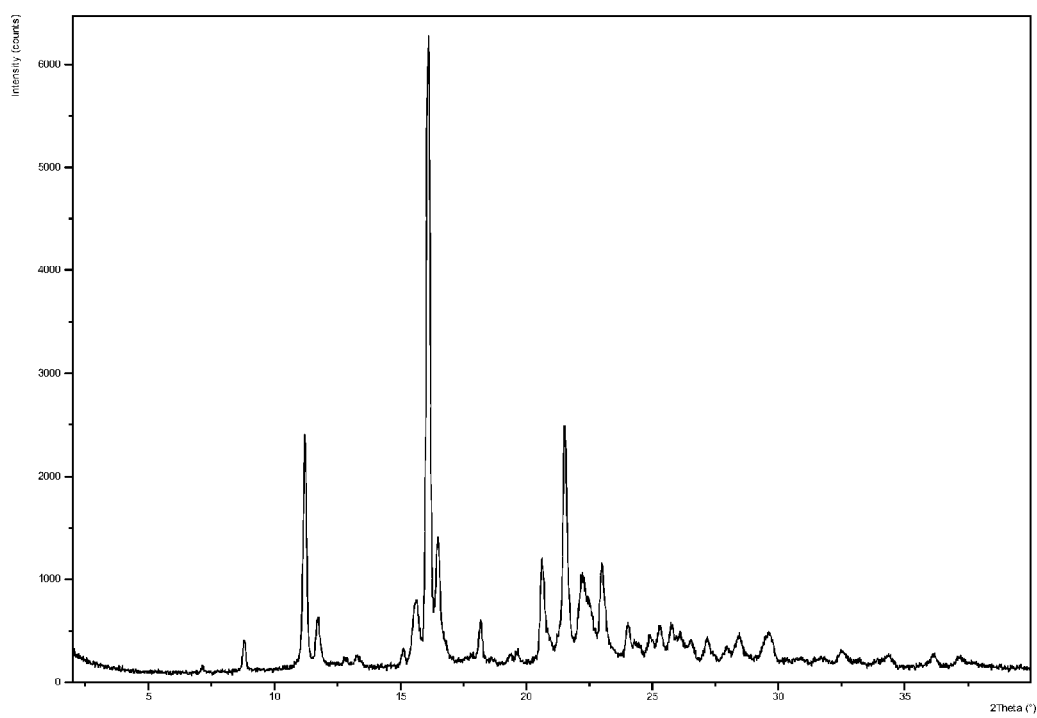
FIG. 3: Shows an XRPD pattern of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 3).

In a further embodiment, there is provided a crystalline form 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 3) characterised by substantially the X-ray powder diffraction (XRPD) pattern as shown in FIG. 3, wherein the XRPD pattern is expressed in terms of 2 theta angles and obtained with a diffractometer using copper Kα-radiation using procedures described herein. The XRPD pattern of anhydrous form 3 shows characteristic 2 theta angle peaks as listed in Example 9 Table 1.

Figure 4:
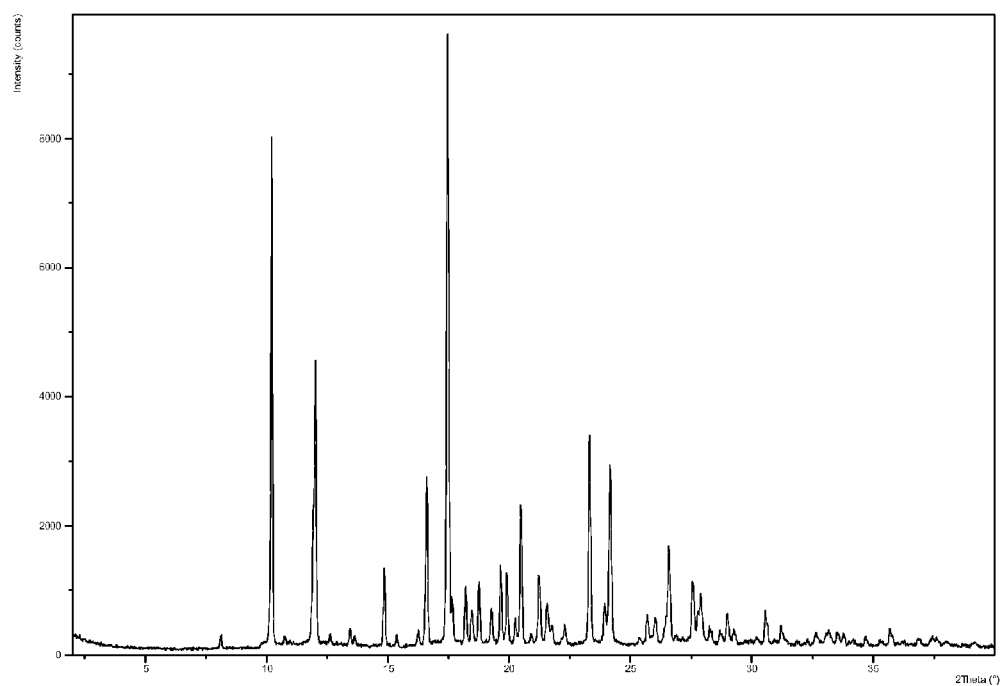
FIG. 4: Shows an XRPD pattern of a crystalline form of 4-(8-methoxy-1-((R)-1-methoxypropan-2-yl)-2-(tetrahydro-2H-pyran-4-yl)-1H-imidazo[4,5-c]$_q$ uinolin-7-yl)-3,5-dimethylisoxazole (hydrate).

In a further embodiment, there is provided a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (hydrate) characterised by substantially the X-ray powder diffraction (XRPD) pattern as shown in FIG. 4, wherein the XRPD pattern is expressed in terms of 2 theta angles and obtained with a diffractometer using copper Kα-radiation using procedures described herein. The XRPD pattern of the hydrate shows characteristic 2 theta angle peaks as listed in Example 9 Table 1.

The invention also provides for the compound of formula (IA) that is to say 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole hydrochloride in crystalline form. Such a crystalline form can be prepared by procedures described herein.

Figure 5:
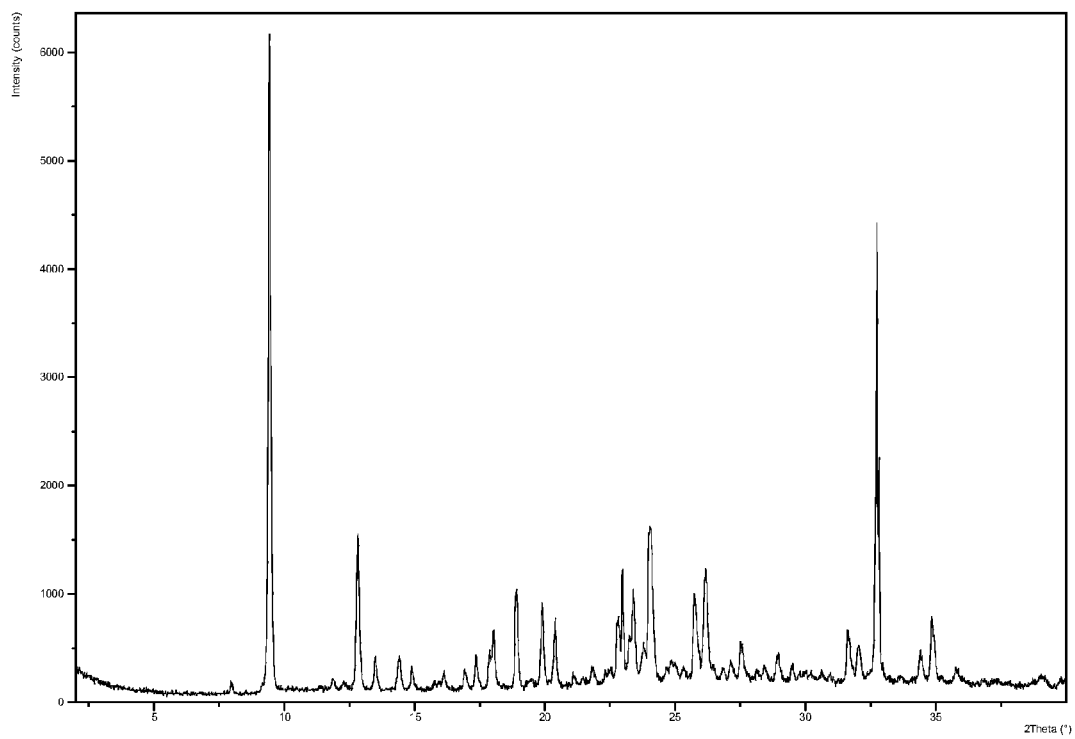
FIG. 5: Shows an XRPD pattern of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole hydrochloride (hydrochloride).

In a further embodiment, there is provided a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole hydrochloride (hydrochloride form 1) characterised by substantially the X-ray powder diffraction (XRPD) pattern as shown in FIG. 5, wherein the XRPD pattern is expressed in terms of 2 theta angles and obtained with a diffractometer using copper Kα-radiation using procedures described herein. The XRPD pattern of this form shows characteristic 2 theta angle peaks as listed in Example 9 Table 1.

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry. Illustrative general synthetic methods are set out below and then specific compounds of formula (I) and pharmaceutically acceptable salts thereof, are prepared in the Examples.

The compound of formula (I) can be prepared from the compound of formula (II) by, for example, heating the compound of formula (II) in acetic acid or p-toluenesulfonic acid in toluene

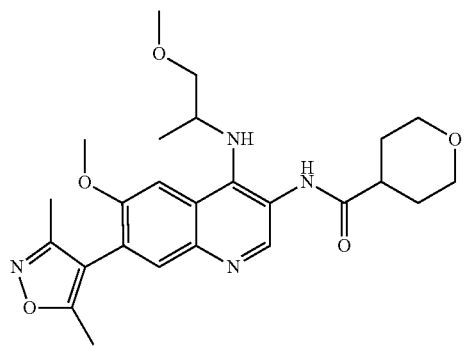
(II)

The compound of formula (II) can be prepared by reaction of the compound of formula (III)

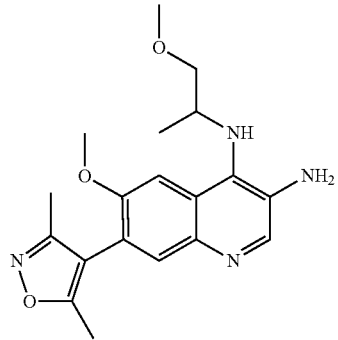 [SMILES: COCC(C)Nc1c([N+](=O)[O-])cnc2cc(-c3c(C)noc3C)c(OC)cc12]
(III)

with a compound of formula (IV) or an activated derivative thereof

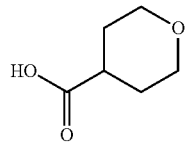
(IV)

A suitable activated derivative of the compound of formula (IV) is the acid chloride. The reaction between the compound of formula (III) and compound of formula (IV) may be carried out in a suitable organic solvent optionally in the presence of a base.

Where the compound of formula (I) is a mixture of isomers the compounds of formula (IA) and formula (IB) can be obtained from the compound of formula (I) using suitable separation techniques which are familiar to those skilled in the art, such as those described herein. Alternatively the compounds of formula (IA) and (IB) may be prepared by a chiral synthesis procedure. By way of illustration, the compound of formula (IA) may be prepared by the procedure set out in Scheme 1.

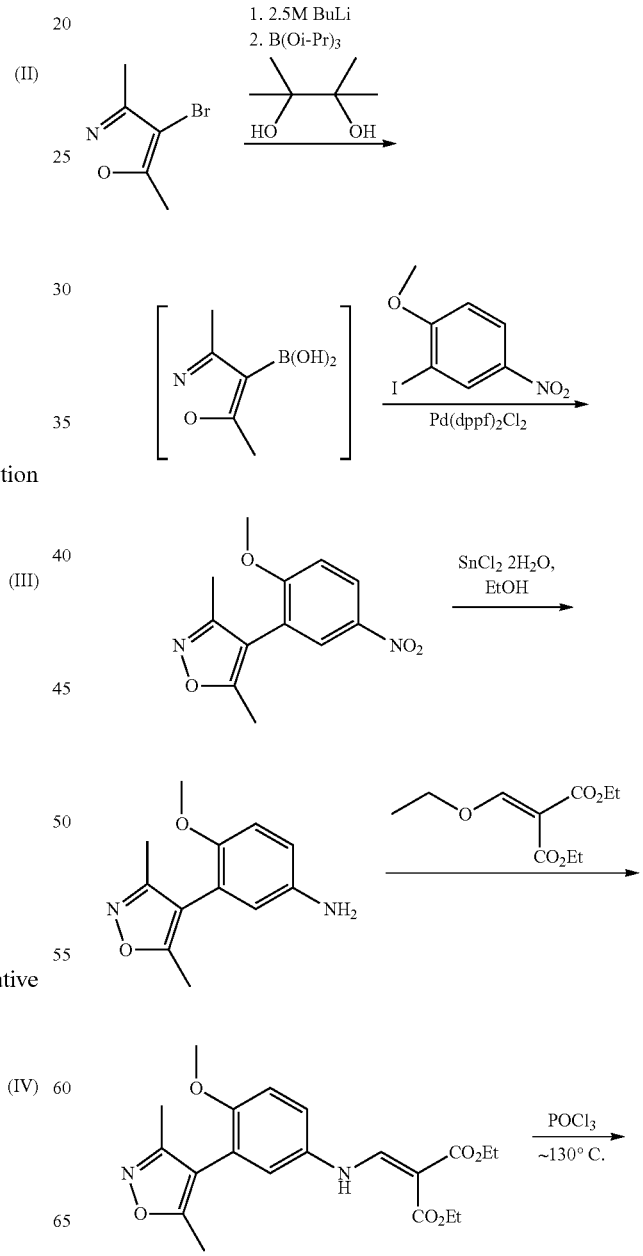

Scheme 1

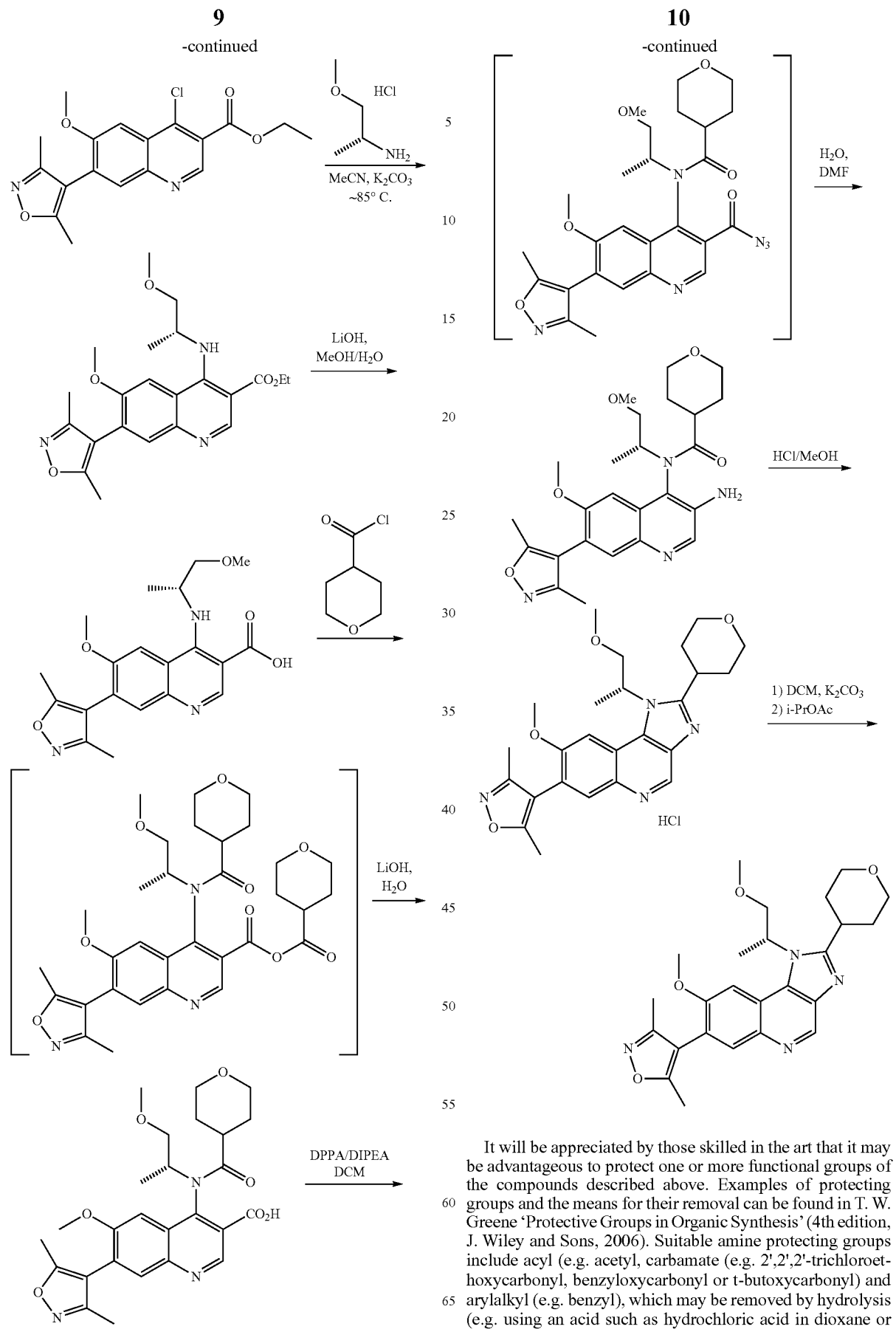

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g.

hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

The compounds of formula (I) and salts thereof are bromodomain inhibitors, and thus are believed to have potential utility in the treatment of diseases or conditions for which a bromodomain inhibitor is indicated. Further, compounds of formula (I) and pharmaceutically acceptable salts thereof (such as the compound of formula (IA) or a pharmaceutically acceptable salt thereof) may have one or more ADMET (absorption, distribution, metabolism, excretion and toxicity) property that makes it particularly suitable.

The present invention thus provides a compound of formula (I) or a pharmaceutically acceptable salt thereof for use in therapy. In one embodiment there is provided a compound of formula (IA) or a pharmaceutically acceptable salt thereof for use in therapy.

The compound of formula (I) or a pharmaceutically acceptable salt thereof can be used in the treatment of diseases or conditions for which a bromodomain inhibitor is indicated. The present invention thus provides a compound of formula (I) or a pharmaceutically acceptable salt thereof for use in the treatment of any diseases or conditions for which a bromodomain inhibitor is indicated. In one embodiment there is provided a compound of formula (IA) or a pharmaceutically acceptable salt thereof for use in the treatment of any diseases or conditions for which a bromodomain inhibitor is indicated. In another embodiment there is provided a compound of formula (I) (such as a compound of formula (1A)) or a pharmaceutically acceptable salt thereof for use in the treatment of chronic auto-immune and/or inflammatory conditions. In a further embodiment there is provided a compound of formula (I) (such as a compound of formula (1A)) or a pharmaceutically acceptable salt thereof for use in the treatment of cancer.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (IA) or a pharmaceutically acceptable salt thereof in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating diseases or conditions for which a bromodomain inhibitor is indicated in a subject in need thereof which comprises administering a therapeutically effective amount of a compound of formula (IA) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, or subject (e.g. a human) that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (kerartoconjunctivitis Sicca), vernal keratoconjunctivitis, atopic keratoconjunctivitis, uveitis (such as anterior uveitis, pan uveitis, posterior uveits, uveitis-associated macula edema).scleritis, diabetic retinopathy, diabetic macula edema, age-related macula dystrophy, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

Bromodomain inhibitors may be useful in the treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis.

Bromodomain inhibitors may be useful in the treatment of viral infections such as herpes virus, human papilloma virus, adenovirus and poxvirus and other DNA viruses.

Bromodomain inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL), In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colarectal cancer.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, human immunodeficiency virus (HIV), cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia. In one embodiment the bromodomain inhibitor is indicated for the treatment of latent HIV infection.

As used herein the reference to the "treatment" of a particular disease or condition includes the prevention or prophylaxis of such a disease or condition.

The term "diseases or conditions for which a bromodomain inhibitor is indicated", is intended to include each of or all of the above diseases or conditions.

The invention further provides for a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. In one embodiment there is provided a pharmaceutical composition comprising a compound of formula (IA) or a pharmaceutically acceptable salt and one or more pharmaceutically acceptable carriers, diluents or excipients. The compounds of formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators includestarch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof, can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for administration (e.g. oral administration) may be designed to provide a modified release profile so as to sustain or otherwise control the release of the therapeutically active agent. A modified release profile of the therapeutically active agent may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Where appropriate, dosage unit compositions for oral administration can be microencapsulated. The composition may be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 to 1000 mg per day or 100 mg to 2500 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof, and may be employed alone or in combination with other therapeutic agents. Combination therapies according to the present invention thus comprise the administration of at least one compound of formula (I) or a pharmaceutically acceptable salt thereof, and the use of at least one other therapeutically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, and at least one other therapeutically active agent.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are desfibed in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulfonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

General Experimental Details

All temperatures referred to are in ° C.

The names of the following compounds have been obtained using the compound naming programme "ACD Name Pro 6.02" or Chem Draw Ultra 12.0.

Abbreviations
1,2-DCE 1,2-dichloroethane
AcOH acetic acid
CHCl$_3$ chloroform
D6-DMSO deuterated dimethylsulfoxide
DCM dichloromethane
DIPEA diisopropylamine
DMSO dimethylsulfoxide DPPA diphenylphosphoryl azide
Et₃N triethylamine
EtOAc ethyl acetate
h hour(s)
HATU O-(7-Azabenzotriazol-1-yl)-N,N,N',N'-tetramethyluronium hexafluorophosphate
HCl hydrochloric acid
i-PrOac isopropylacetate
i-Pr₂O diisopropyl ether
LCMS liquid chromatography-mass spectrometry
LiOH lithium hydroxide
M molar (concentration)
MeCN acetonitrile
MeOH methanol
min minute(s)
N normal (concentration)
Na₂CO₃ sodium carbonate
Na₂SO₄ sodium sulphate
Pd/C palladium on carbon
Rt retention time
TBME tertiary butyl methyl ether
TFA trifluoroacetic acid
THF tetrahydrofuran
UPLC Ultra performance liquid chromatograpy
LCMS Methodology
Method Formate
LC Conditions The UPLC analysis was conducted on an Acquity UPLC BEH C18 column (50 mm×2.1 mm, i.d. 1.7 µm packing diameter) at 40° C.

The solvents employed were:
　A=0.1% v/v solution of formic acid in water
　B=0.1% v/v solution of formic acid in acetonitrile
The gradient employed was:

| Time (min) | Flow rate (ml/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was a summed signal from wavelength of 210 nm to 350 nm.
MS conditions
MS: Waters ZQ
Ionisation mode: Alternate-scan positive and negative electrospray
Scan range: 100 to 1000 AMU
Scan time: 0.27 sec
Inter scan: delay 0.10 sec
NMR
Spectra were run on a 400 mHz NMR machine at either 302 K or for VT spectra at 392-393 K.

Intermediate 1

7-(3,5-dimethylisoxazol-4-yl)-6-methoxy-N-(1-methoxypropan-2-yl)-3-nitroquinolin-4-amine

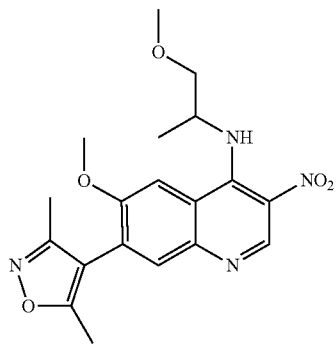

To a solution of 4-(4-chloro-6-methoxy-3-nitroquinolin-7-yl)-3,5-dimethylisoxazole (Manchester Organics) (20 g, 59.9 mmol) in 1,4-dioxane (200 ml) was added 1-methoxypropan-2-amine (31.6 ml, 300 mmol) and the reaction mixture heated at 70° C. for 1.5 h. The solvent was removed under reduced pressure and the resulting solid partitioned between ethyl acetate (3×750 ml) and water (750 ml). The organic layers were combined, dried (hydrophobic frit) and evaporated under reduced pressure to give 7-(3,5-dimethylisoxazol-4-yl)-6-methoxy-N-(1-methoxypropan-2-yl)-3-nitroq uinolin-4-amine (25.8 g), which was used without further purification in the subsequent step.
NMR (D₆-DMSO): OH 9.03 (s, 1H), 8.63 (d, 1H), 7.83 (s, 1H), 7.81 (s, 1H), 4.39 (m, 1H), 3.97 (s, 3H), 3.54 (m, 2H), 3.27 (s, 3H), 2.34 (s, 3H), 2.15 (s, 3H), 1.41 (d, 3H).
LCMS (formate): Rt=0.97 min, MH⁺387.

Intermediate 2

7-(3,5-dimethylisoxazol-4-yl)-6-methoxy-N4-(1-methoxypropan-2-yl)quinoline-3,4-diamine

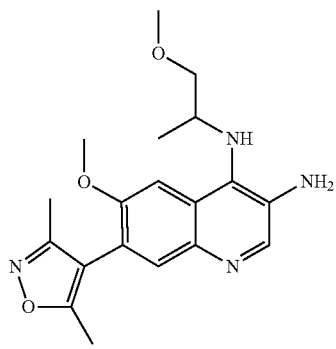 [SMILES: COCC(C)Nc1c(N)cnc2cc(-c3c(C)noc3C)c(OC)cc12]

7-(3,5-Dimethylisoxazol-4-yl)-6-methoxy-N-(1-methoxypropan-2-yl)-3-nitroquinolin-4-amine (for a preparation see Intermediate 1)(25.8 g, 66.8 mmol) was dissolved in a mixture of ethyl acetate (1000 ml) and DMSO (50 ml) and the solution was hydrogenated using a flow-hydrogenation apparatus (H-cube™) (settings: 20° C., 1 bar, 1 ml/min flow rate) and a 10% Pd/C CatCart 70 catalyst cartridge. The catalyst cartridge was changed whenever it became blocked. The reaction mixture was evaporated under reduced pressure and partitioned between ethyl acetate (750 ml) and water (3×750 ml). The aqueous layers were combined and extracted with ethyl acetate (750 ml). The organic layers were were combined, dried (hydrophobic frit) and evaporated under reduced pressure. The residue was dissolved in DCM and applied to a silica cartridge (100 g). The cartridge was eluted with a 2M ammonia in methanol/DCM gradient (0-4%). The appropriate fractions were combined and evaporated under reduced pressure to give 7-(3,5-dimethylisoxazol-4-yl)-6-methoxy-N⁴-(1-methoxypropan-2-yl)quinoline-3,4-diamine and recovered 7-(3,5-dimethylisoxazol-4-yl)-6-methoxy-N-(1-methoxypropan-2-yl)-3-nitroquinolin-4-amine (6.5 g)

The recovered starting material was dissolved in ethyl acetate (250 ml) and the solution was hydrogenated using a flow-hydrogenation apparatus (H-cube™) (settings: 20° C., 1 bar, 1 ml/min flow rate) and 10% Pd/C CatCart 70 catalyst cartridge. The reaction mixture was evaporated under reduced pressure and the residue was dissolved in DCM and applied to a silica cartridge (100 g). The cartridge was eluted with a 2M ammonia in methanol/DCM gradient (0-4%). The appropriate fractions were combined and evaporated under reduced pressure to give 7-(3,5-dimethylisoxazol-4-yl)-6-methoxy-N4-(1-methoxypropan-2-yl)quinoline-3,4-diamine The batches of product were combined to give 7-(3,5-dimethylisoxazol-4-yl)-6-methoxy-N4-(1-methoxypropan-2-yl)quinoline-3,4-diamine (15.6 g, 43.8 mmol, 65.6% yield) as a sticky dark brown gum.

NMR (D₆-DMSO): δH 8.29 (s, 1H), 7.55 (s, 1H), 7.45 (s, 1H), 5.13 (s, 2H), 4.48 (d, 1H), 3.88 (s, 3H), 3.54 (m, 1H), 3.35 (m, 2H), 3.29 (s, 3H), 2.30 (s, 3H), 2.10 (s, 3H), 1.18 (d, 3H). LCMS (formate): Rt 0.73 min, MH⁺357

Intermediate 3

N-(7-(3,5-dimethylisoxazol-4-yl)-6-methoxy-4-((1-methoxypropan-2-yl)amino)quinolin-3-yl)tetrahydro-2H-pyran-4-carboxamide

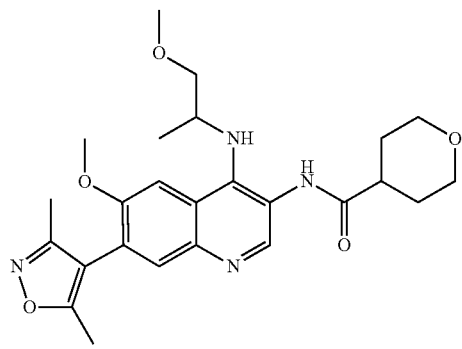 [SMILES: COCC(C)Nc1c(NC(=O)C2CCOCC2)cnc2cc(-c3c(C)noc3C)c(OC)cc12]

A solution of 7-(3,5-dimethylisoxazol-4-yl)-6-methoxy-N4-(1-methoxypropan-2-yl)quinoline-3,4-diamine (for a preparation see Intermediate 2) (9.1 g) in DCM (300 ml) was treated with pyridine (30 ml) and tetrahydro-2H-pyran-4-carbonyl chloride (5.0 ml) and the solution stirred under nitrogen at ambient temperature for 3.5 h and then left standing overnight (ambient temperature, under nitrogen). The volatiles were evaporated in vacuo and the residue partitioned between DCM and water. The organic phase was washed with water ×2 and the combined aqueous extracted with DCM. The combined organic phases were washed with brine, dried (hydrophobic frit) and reduced to dryness in vacuo. The combined aqueous including the brine wash (~pH4) was basified with solid sodium hydrogen carbonate and the aqueous extracted with DCM x2. The organic fractions were dried (hydrophobic frit), combined with the previous material and reduced to dryness in vacuo to give a brown foam. This foam was further dried in vacuo, triturated with diethyl ether, the suspension chilled (ice/water bath) and the solid isolated by filtration. The solid was washed with a little diethyl ether and air-dried to give N-(7-(3,5-dimethylisoxazol-4-yl)-6-methoxy-4-((1-methoxypropan-2-yl)amino)quinolin-3-yl)tetrahydro-2H-pyran-4-carboxamide as a beige solid (11.95 g, 100%).

NMR (D₆-DMSO): δH 9.49 (s, 1H), 8.38 (s, 1H), 7.70 (s, 1H), 7.63 (s, 1H), 5.33 (d, 1H), 3.96-3.90 (m, 6H), 3.43-3.28 (m partially obscured by water, 7H), 2.69 (m, 1H), 2.32 (s, 3H), 2.12 (s, 3H), 1.81-1.67 (m, 4H), 1.19 (d, 3H). LCMS (formate): Rt 0.69 mins, MH⁺469.

Example 1

4-(8-methoxy-1-(1-methoxypropan-2-yl)-2-(tetrahydro-2H-pyran-4-yl)-1H-imidazo[4,5-c]quinolin-7-yl)-3,5-dimethylisoxazole

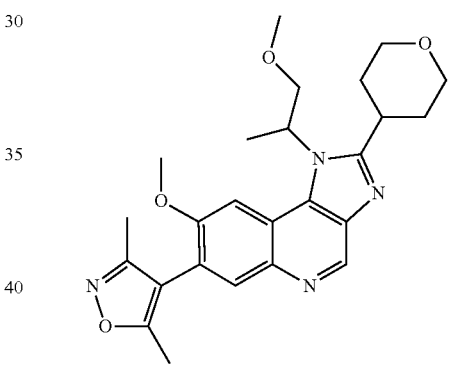

A suspension of N-(7-(3,5-dimethylisoxazol-4-yl)-6-methoxy-4-((1-methoxypropan-2-yl)amino)quinolin-3-yl)tetrahydro-2H-pyran-4-carboxamide (for a preparation see Intermediate 3) (29.4 g, 62.7 mmol) in acetic acid (250 ml, 62.7 mmol) was heated at 120° C. for 2 h. 3 Å molecular sieves (20 g) were added and heating continued for 3.5 h. Further 3 Å molecular sieves (20 g, oven dried) were added and heating was continued overnight. Further 3 Å molecular sieves (20 g, oven dried) were added and heating continued for a further 24 h.

The reaction mixture was allowed to cool to room temperature, and the solid removed by filtration. The residue and filtrate were combined and evaporated under reduced pressure. Water (3 l) was added, and the resultant slurry was neutralised by the slow addition of solid sodium hydrogen carbonate. The aqueous slurry was extracted with DCM (3×1 l), and the organic phases were combined, dried (hydrophobic frit) and evaporated under reduced pressure to give a brown gum.

The gum was dissolved with warming and sonication in a minimal quantity of DCM. The solution was applied to a silica column (750 g) which had been pre-wetted with DCM. The column was eluted with a gradient of [2 M ammonia in methanol, methanol (3:1)]/DCM (0-~8%). The product fractions were combined and reduced to dryness under reduced pressure to give a cream foam/glass (13.027 g).

The mixed product fractions were combined and reduced to dryness under reduced pressure to give a deep yellow oil. This oil was dissolved in diethyl ether and the volatiles evaporated in vacuo to give a yellow solid. The solid was triturated with diethyl ether, the solid isolated by filtration and washed with diethyl ether (×2) to give 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole.

The cream foam/glass was triturated with diethyl ether/ethyl acetate, the mixture reduced to dryness under reduced pressure and the trituration was repeated with diethyl ether. The previous product fraction was added to the suspension and the mixture aged overnight. The solid was isolated by filtration and washed with diethyl ether to give 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole as a cream solid. The solid was dried in vacuo and retriturated with diethyl ether with stirring over ~30 min. The solid was isolated by filtration and washed with diethyl ether. The solid was dried in vacuo to give 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole as a white solid (11.73 g).

VT NMR ($D_6$-DMSO): δH 9.04 (s, 1H), 7.99 (s, 1H), 7.74 (s, 1H), 5.45 (m, 1H), 4.14 (m, 1H), 4.06-4.01 (m, 6H), 3.62 (m, 2H), 3.47 (m, 1H), 3.28 (s, 3H), 2.35 (s, 3H), 2.17 (s, 3H), 2.09 (m, 2H), 1.92 (m, 2H), 1.83 (d, 3H). LCMS (formate): Rt 0.76 min, MH$^+$451.

Example 1

Alternative Preparation 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole A mixture of N-(7-(3,5-dimethylisoxazol-4-yl)-6-methoxy-4-(((1-methoxypropan-2-yl)amino)quinolin-3-yl)tetrahydro-2H-pyran-4-carboxamide (for a preparation see Intermediate 3) (11.95 g, 25.5 mmol) and p-toluenesulfonic acid (1.2 g, 25.5 mmol) in toluene (250 ml) was heated under nitrogen at reflux using a Dean-Stark apparatus for 3 days. Further p-toluenesulfonic acid (0.2 g, 4.3 mmol) was added and heating continued overnight. Water (750 ml) was added, and the mixture basified to pH 8 using saturated aqueous sodium hydrogen carbonate solution. The aqueous was extracted with ethyl acetate (3×750 ml), the organic layers combined, dried (hydrophobic frit) and evaporated under reduced pressure. The residual solid was triturated in ether (~200 ml), sonicated briefly. The majority of the solid appeared to be a fine powder. The fine powder suspended in the ether was decanted, the solid isolated by filtration, and dried in a vacuum oven to give crude 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole (6.3 g). This material was triturated in ether (~100 ml), sonicated briefly, and stood overnight at room temperature. The solid was isolated by filtration and dried in a vacuum oven 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole (4.9 g, 10.88 mmol, 42.6% yield). LCMS (formate): Rt 0.75 min, MH$^+$451.

The clumped solid left over from the decanting was triturated in ether (100 ml), sonicated for 15 min, and stood at room temperature for 3 days. The solid was isolated by filtration and dried in a vacuum oven to give 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole (3.6 g, 7.99 mmol, 31.3% yield). LCMS (formate): Rt 0.76 min, MH$^+$451.

Example 2

4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole

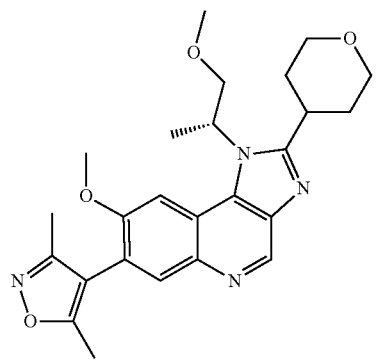

Chiral resolution of 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole was carried out using the following conditions:
Column: Chiralpak AD-H (250×30 mm, 5 micron) [ADH10029-01]
Flowrate: 45 ml/min
Detection: UV DAD (300 nm (bandwidth 180 nm, reference 550 nm (bandwidth 100 nm)).
Mobile Phase A: n-Hexane (10 ml of isopropylamine per Winchester (2.5 L))
Mobile Phase B: Ethanol (10 ml of isopropylamine per Winchester (2.5 L))
Isocratic system—85:15 mobile phase A:B
Run time—ca. 35 min
4-(8-methoxy-1-(1-methoxypropan-2-yl)-2-(tetrahydro-2H-pyran-4-yl)-1H-imidazo[4,5-c]quinolin-7-yl)-3,5-dimethylisoxazole (500 mg) was suspended in ethanol and ethylene glycol (10 ml:5 ml) and then sonicated and heated to aid solution. Isopropylamine (1 ml) was then added. This working solution was warmed on a hotplate (60° C.) whilst purification was ongoing to keep in solution. Injections (1.5 ml) were made using autosampler. Fractions collected on time basis using funnel bed fraction collector between 28 min and 35 min. The combined fraction solutions were evaporated to dryness using a rotary evaporator (30° C. bath temp) and the residue transferred to a tared 20 ml glass vial using ethanol (ca 12 ml). The ethanol was evaporated under a stream of nitrogen gas (room temp).

4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (1.16 g) isolated using the above process was triturated with diethyl ether (—3 ml) over ~4 h at ambient temperature. The solid was isolated by filtration, washed with diethyl ether and dried in vacuo to give 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole as a cream solid (0.96 g).

VT NMR (D$_6$-DMSO): δH 9.03 (s, 1H), 7.98 (s, 1H), 7.74 (s, 1H), 5.43 (m, 1H), 4.13 (m, 1H), 4.04-4.00 (m, 6H), 3.61 (m, 2H), 3.46 (m, 1H), 3.28 (s, 3H), 2.35 (s, 3H), 2.16 (s, 3H), 2.08 (m, 2H), 1.92 (m, 2H), 1.82 (d, 3H). LCMS (formate): Rt 0.76 min, MH$^+$451.

Example 3

4-(8-methoxy-1-((S)-1-methoxypropan-2-yl)-2-(tetrahydro-2H-pyran-4-yl)-1H-imidazo[4,5-c]quinolin-7-yl)-3,5-dimethylisoxazole

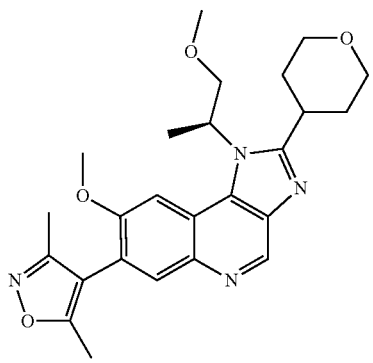

Chiral resolution of 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole was carried out using the following conditions:
Column: Chiralpak AD-H (250×30 mm, 5 micron) [ADH10029-01]
Flowrate: 45 ml/min
Detection: UV DAD (300 nm (bandwidth 180 nm, reference 550 nm (bandwidth 100 nm)).
Mobile Phase A: Heptane
Mobile Phase B: Ethanol
Isocratic system—85:15 mobile phase A:B
Run time—ca. 35 min
4-(8-methoxy-1-(1-methoxypropan-2-yl)-2-(tetrahydro-2H-pyran-4-yl)-1H-imidazo[4,5-c]quinolin-7-yl)-3,5-dimethylisoxazole (85 mg) was dissolved in ethanol (ca. 4 ml) with heating and sonication. Injections (400 µl) were then made via plastic syringe. The fractions between 24 min and 26.5 min were collected and the combined fraction solutions were evaporated to dryness using a rotary evaporator (30° C. bath temp). The residue was transferred to a tared glass vial using ethanol (ca 12 ml). The solvent was then removed by evaporation under a stream of nitrogen gas (room temp) to give 4-(8-methoxy-1-((S)-1-methoxypropan-2-yl)-2-(tetrahydro-2H-pyran-4-yl)-1H-imidazo[4,5-c]quinolin-7-yl)-3,5-dimethylisoxazole (38 mg).

VT NMR (D$_6$-DMSO): δH 9.00 (s, 1H), 7.95 (s, 1H), 7.72 (s, 1H), 5.41 (m, 1H), 4.10 (m, 1H), 4.03-3.97 (m, 6H), 3.59 (m, 2H), 3.45 (m, 1H), 3.26 (s, 3H), 2.32 (s, 3H), 2.13 (s, 3H), 2.07 (m, 2H), 1.90 (m, 2H), 1.80 (d, 3H). LCMS (formate): Rt 0.73 min, MH$^+$451.

Example 4

Preparation of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 1)

4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (for a preparation see Example 2 or reaction scheme 1, 18.87 g) was dissolved in isopropyl acetate (95 mL) at reflux and then allowed to cool to 20° C. over 1 hr. Cyclohexane (190 mL) was then added over 1 hr and the resultant slurry was aged for 1 hr. The slurry was then filtered and washed with 2:1 cyclohexane:isopropylacetate (30 mL) and then cyclohexane (30 mL) before being pulled dry. The cake was then oven dried overnight at 40° C. under vacuum. An XRPD was recorded on this material (see Example 9).

Example 5

Preparation of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 2)

A pre-mixed solution of isopropyl acetate (211 mL) and cyclohexane (422 mL) was added to 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (for a preparation see Example 2 or reaction scheme 1, 42.19 g, 94 mmol). The resulting suspension was stirred for 24 hours, filtered, the resulting solid washed (1× cyclohexane:isopropyl acetate (2:1, 180 ml), 1× cyclohexane (180 ml), 1×TBME (180 ml)), pulled to dryness and dried in vacuo at 40° C. to constant weight giving an almost white solid (90% yield). An XRPD was recorded on this material (see Example 9).

Example 6

Preparation of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (hydrate)

A pre-mixed solution of ethanol (2.000 mL) and water (8.00 mL) was added to 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (for a preparation see Example 2 or reaction scheme 1, 1.00 g, 2.220 mmol) and the resulting suspension stirred overnight. The suspension was filtered, washed (2× water, 2×TBME), pulled to dryness under vacuum and dried in vacuo at 40° C. to give a white powder. An XRPD was recorded on this material (see Example 9).

Example 7

Preparation of a crystalline form of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole (anhydrous form 3)

4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole hydrate (for a preparation see Example 6, 860 mg, 1.835 mmol) was heated at 135° C. at 9 mbar overnight. An XRPD was recorded on this material (see Example 9).

Example 8

Preparation of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole hydrochloride (hydrochloride)

In a first reactor a solution of 7-(3,5-dimethylisoxazol-4-yl)-6-methoxy-4-(N—((R)-1-methoxypropan-2-yl)tetrahydro-2H-pyran-4-carboxamido)quinoline-3-carboxylic acid (for a preparation see Scheme 1, 23.3 kg) in DCM (113 kg) and DIPEA (3.8 kg) was combined with acetonitrile (61.6 kg) and di-iso-propylamine (12.8 kg) the mixture was cooled to between −10 and −3° C. Diphenylphosphoryl azide (19.0 kg) was added maintaining the temperature between −10 and −3° C. and the reaction stirred at this temperature. Further diphenylphosphoryl azide (2.4 kg) was added maintaining the temperature between −10 and −3° C. and the reaction stirred at this temperature to form a first solution.

In a second reactor dimethyl formamide (144 kg) and water (72 kg) were heated to 90-100° C. The first solution was added maintaining the temperature between 85-100° C., reactor 1 was rinsed with acetonitrile (7 kg) and the rinse added to the second reactor maintaining the temperature between 85-100° C. The mixture was stirred at this temperature and then cooled to 20-30° C. The pH was adjusted to pH=10 with 30% wt aqueous sodium hydroxide solution (10.4 kg) maintaining the temperature between 20-30° C. Dichloromethane (315 kg) and water (351 kg) were charged, the layers were separated and the aqueous layer extracted with dichloromethane (315 kg). The combined organic layers were washed with water (234 kg). Water (234 kg) was charged to the organic layer, the mixture stirred, sodium chloride (80 kg) added and the layers separated. The organic layer was concentrated under reduced pressure below 30° C., methanol (201 kg) was charged and the solution concentrated under reduced pressure below 50° C. Further methanol (199 kg) and 4M hydrochloric acid in methanol (68.5 kg) were charged maintaining the temperature 20-30° C. and the reaction was stirred at this temperature. The mixture was concentrated under reduced pressure below 50° C. and acetonitrile (104 kg) charged. The mixture was concentrated under reduced pressure below 50° C. and further acetonitrile (97 kg) charged. The mixture was concentrated under reduced pressure below 50° C. and further acetonitrile (116 kg) charged. The mixture was evaporated under reduced pressure below 50° C. and further acetonitrile (103.0 kg) was charged. The mixture was cooled to between −5-0° C. and stirred at this temperature. The slurry was centrifuged in two portions, each portion was washed with acetonitrile (9 kg) to give the title compound (33.40 kg, 99.3% purity) as a wet cake.

Example 9

X-ray Powder Diffraction (XRPD) Studies on Crystalline Forms of 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole as a free base and as a hydrochloride salt The data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

Peak positions were measured using Highscore software. The margin of error is approximately ±0.1° 2θ for each of the peak assignments. Peak intensities may vary from sample to sample due to preferred orientation.

Table 1 shows characteristic XRPD peak positions and d-spacings for crystalline form of the compound 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole as a free base and as a hydrochloride salt.

TABLE 1

| Free base anhydrous form 1 | | Free base anhydrous form 2 | | Free base anhydrous form 3 | | Free base Hydrate | | hydrochloride | |
| --- | --- | --- | --- | --- | --- | --- | --- | --- | --- |
| 2θ/° | d-spacing/Å | 2θ/° | d-spacing/Å | 2θ/° | d-spacing/Å | 2θ/° | d-spacing/Å | 2θ/° | d-spacing/Å |
| 7.9 | 11.1 | 6.5 | 13.6 | 8.8 | 10.0 | 8.1 | 10.9 | 9.4 | 9.4 |
| 8.5 | 10.4 | 10.8 | 8.2 | 11.2 | 7.9 | 10.2 | 8.7 | 12.8 | 6.9 |
| 10.7 | 8.3 | 13.0 | 6.8 | 11.7 | 7.5 | 12.0 | 7.4 | 13.5 | 6.6 |
| 12.1 | 7.3 | 14.0 | 6.3 | 16.1 | 5.5 | 14.8 | 6.0 | 14.4 | 6.1 |
| 12.7 | 7.0 | 15.3 | 5.8 | 16.5 | 5.4 | 16.6 | 5.3 | 14.9 | 5.9 |
| 13.9 | 6.4 | 17.7 | 5.0 | 18.2 | 4.9 | 17.5 | 5.1 | 17.4 | 5.1 |
| 15.9 | 5.6 | 19.3 | 4.6 | 20.6 | 4.3 | 18.2 | 4.9 | 18.9 | 4.7 |
| 16.7 | 5.3 | 20.8 | 4.3 | 21.5 | 4.1 | 18.8 | 4.7 | 19.9 | 4.5 |
| 18.8 | 4.7 | 21.6 | 4.1 | 23.0 | 3.9 | 19.7 | 4.5 | 20.4 | 4.4 |
| 21.0 | 4.2 | 22.6 | 3.9 | | | 20.5 | 4.3 | 24.0 | 3.7 |
| 22.7 | 3.9 | 25.3 | 3.5 | | | 23.3 | 3.8 | 25.7 | 3.5 |
| 24.3 | 3.7 | 27.2 | 3.3 | | | 24.1 | 3.7 | 26.2 | 3.4 |
| 29.1 | 3.1 | | | | | 26.6 | 3.4 | 32.7 | 2.7 |
| 29.8 | 3.0 | | | | | | | | |

Biological Test Methods

The compounds of formula (I) may be tested in one or more of the following assays.

Time Resolved Fluorescence Resonance Energy Transfer (TR-FRET) Assay

The binding of the compounds of formula (I) to Bromodomains BRD2, BRD3 and BRD4 was assessed using a time resolved fluorescent resonance energy transfer binding assay, that measures the binding of an acetylated histone peptide to the bromodomain protein.

The bromodomain protein, histone peptide and a variable concentration of test compound are incubated together to reach thermodynamic equilibrium. The assay is configured such that in the absence of test compound the bromodomain and peptide are significantly bound (~30%) and in the presence of a sufficient concentration of a potent inhibitor this interaction is disrupted leading to a measurable drop in fluorescent resonance energy transfer.

```
Histone Peptide:
H-Ser-Gly-Arg-Gly-Lys(Ac)-Gly-Gly-Lys(Ac)-Gly-Leu-
Gly-Lys(Ac)-Gly-Gly-Ala-Lys(Ac)-Arn-His-Gly-Ser-
Gly-Ser-Lys(Biotin)-OH. 3TFA
```

The protected peptide was assembled on a solid-phase synthesiser using preloaded Wang resin and utilising standard Fmoc synthesis protocols. The C-terminal lysine was protected by a hyper acid-labile group allowing for its selective removal at the end of the assembly and attachment of the biotin. The crude peptide was obtained after cleavage from the resin with a mixture of trifluoroacetic acid (TFA), triisopropylsilane and water (95:2.5:2.5) for 3 h at room temperature and was then purified using a C18 reverse-phase column utilising a 0.1% TFA-buffered water/acetonitrile gradient. The resulting fractions were analysed and fractions which were >95% pure by analytical HPLC and giving the correct mw (by MALDiTOF mass spectroscopy) were pooled and freeze dried. The final material was analysed by HPLC to confirm purity.

Protein Production:

Recombinant Human Bromodomains (BRD2 (1-473), BRD3 (1-435) and BRD4 (1-477)) were expressed in *E. coli* cells (in pET15b vector) with a six-His tag at the N-terminal. The His-tagged Bromodomain was extracted from *E. coli* cells using sonication and purified using a nickel sepharose 6FF column, the proteins were washed and then eluted with 50 mM Tris-Hcl pH8.0. 300 mM NaCl, 1 mM 6-mercaptoethanol and 20 mM Imidazole. Further purification was performed by affinity chromatography on a H isTRAP HP column, eluting with a linear 0-500 mM sodium chloride gradient, over 20 column volumes. Final purification was completed by Superdex 200 prep grade size exclusion column. Purified protein was stored at −80 C in 20 mM HEPES pH 7.5 and 100 mM NaCl. Protein identity was confirmed by peptide mass fingerprinting and predicted molecular weight confirmed by mass spectrometry.

Protocol for Bromodomain BRD 2, 3 and 4 Assays:

All assay components were dissolved in buffer composition of 50 mM HEPES pH7.4, 50 mM NaCl and 0.5 mM CHAPS. The final concentration of bromodomain proteins were 100 nM and the histone peptide was 300 nM, these components are premixed and allowed to equilibrate for 1 hour in the dark. 8 µl of this reaction mixture was added to all wells containing 50 nl of various concentrations of test compound or DMSO vehicle (0.5% final) in Greiner 384 well black low volume microtitre plates and incubated in dark for 60 mins at room temperature. 2 µl of detection mixture containing anti-6his XL665 labeled antibody and streptavidin labeled with europium cryptate was added to all wells and a further dark incubation of at least 30 mins was performed. Plates were then read on the Envision platereader, ($\lambda$ex=317 nm, donor $\lambda$EM=615 nm; acceptor $\lambda$EM=665 nm; Dichroic LANCE dual). Time resolved fluorescent intensity measurements were made at both emission wavelengths and the ratio of acceptor/donor was calculated and used for data analysis. All data was normalized to the mean of 16 high and 16 low control wells on each plate. A four parameter curve fit of the following form was then applied:

$$y=a+((b-a)/(1+(10^x/10^c)^d)$$

Where 'a' is the minimum, 'b' is the Hill slope, 'c' is the pIO50 and 'd' is the maximum.

Examples 1-3 were tested in all of the BRD2, BRD3 and BRD4 assays described above and were found to have a pIC$_{50}$ in the range 6.5-7.5 in each assay.

Measurement of LPS induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 µl of the diluted stocks is added to a 96 well plate. Following addition of whole blood (130 ul) the plates are incubated at 37 degrees (5% $CO_2$) for 30 min before the addition of 10 µl of 2.8 ug/ml LPS, diluted in complete RPMI 1640 (final concentration=200 ng/ml), to give a total volume of 140 µl per well. After further incubation for 24 hours at 37 degrees, 140 µl of PBS are added to each well. The plates are sealed, shaken for 10 minutes and then centrifuged (2500 rpm×10 min). 100 µl of the supernatant are removed and IL-6 levels assayed by immunoassay (typically by MesoScale Discovery technology) either immediately or following storage at −20 degrees. Concentration response curves for each compound was generated from the data and an 10$_{50}$ value was calculated Examples 1 and 2 were tested in this assay and were found to have a 00$_{50}$ in the range 6.0-7.0.

These data demonstrate that bromodomain inhibitors tested in the above whole blood assay inhibited the production of key inflammatory mediator IL-6.

In Vivo Mouse Model to Demonstrate Modulation of Pro-Inflammatory Response

Male CD1 mice (25-30 g, n=4 per group) received a single i.v. bolus injection of LPS (100 pg/kg) via the tail vein 1 h after pre-treatment with a single oral administration of either vehicle (1% (w/v) methylcellulose in sterile water) or the test compound (3, 10 and 30 mg/kg). Serial blood samples were obtained from the tail vein by direct venepuncture at various time points up to 5 h post-LPS administration for analysis of IL-6 and the test compound concentrations by Meso Scale Discovery (MSD) analysis and LC-MS/MS respectively.

In vehicle control mice, i.v. LPS induced a time-dependent increase in serum IL-6 concentrations, while mice pre-treated orally with the compound of Example 2 (3, 10 and 30 mg/kg) had reduced maximum ($C_{max}$) IL-6 levels by 46%, 79%, 73% respectively, and reduced total exposures (AUC) of IL-6 by 35%, 70%, 63% respectively. This reduction in IL-6 is comparable to the maximal reduction observed with the positive control dexamethasone, i.e.: 73% and 70% reduction in IL-6 $C_{max}$ and AUC, respectively.

These data demonstrate that the compound of Example 2 tested in the above assay reduced LPS-induced systemic IL-6 levels in the mouse following a single oral administration and consequently may have utility as an anti-inflammatory agent.

Oncology Cell Growth Assay

Human cell lines (n=80 comprising cell lines described in Table 2 below) were cultured in RPMI-1640 containing 10% fetal bovine serum, 1000 viable cells per well were plated in 384-well black flat bottom polystyrene plates (Greiner #781086) in 48 µl of culture media. All plates were placed at 5% $CO_2$, 37° C. overnight. The following day one plate was harvested with CellTiter-Glo (CTG, Promega #G7573) for a time equal to 0 (TO) measurement and compound (20 point titration from 14.7 uM to 7 µM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results are expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin–T0 value is determined by subtracting the T0 value (100%) from the Ymin value (%) determined from the fit of the concentration response curve. Values from the wells with no cells were subtracted from all samples for background correction.

The compound of Example 2 was tested in accordance with the above procedure and found to have the $gIC_{50}$ as shown in Table 2.

TABLE 2

| Cell line type | n (number of lines) | $gIC_{50}$ |
| --- | --- | --- |
| Multiple myeloma | 16 | 1.1 to >29326 nM (median 414 nM), with 15 out of 16 cell lines in the range 1.1 to 2000 nM |
| Small cell lung cancer (SCLC) | 38 | 76 to >29326 nM (median 538 nM), with 35 of the 38 cell lines in the range 76 to 2500 nM |
| Cervical cancer | 4 | 266-847 nM |
| NUT-midline carcinoma | 2 | 59-66 nM |
| Neuroblastoma | 12 | 25-435 nM (median 193 nM) |
| Esophageal | 8 | 208-1544 nM (median 759 nM) |

The compound of Example 2 was also tested in accordance with an analogous procedure using 96 well plates along with appropriate modifications to volumes and concentrations that would be apparent to those skilled in the art. The compound of Example 2 was tested and found to have the $gIC_{50}$ as shown in Table 3.

TABLE 3

| Cell line type | n (number of lines) | $gIC_{50}$ |
| --- | --- | --- |
| Acute monocytic leukemia | 1 | 123 nM |
| Acute promyelocytic leukemia | 1 | 141 nM |
| Cutaneous T cell lymphoma | 1 | 162 nM |
| Burkitt's lymphoma | 3 | 181-807 nM |
| Chronic myeloid leukemia | 1 | 776 nM |
| Breast cancer (ductal) | 1 | 537 nM |
| Ovarian carcinoma | 1 | 707 nM |

These data demonstrate that the compound of Example 2 tested in the above assay inhibited cell growth in a panel of oncology cell lines and may therefore have utility in the treatment of one or more cancers.

All publications, including but not limited to patents and patent applications, cited in this specification are herein incorporated by reference as if each individual publication were specifically and individually indicated to be incorporated by reference herein as though fully set forth.

What is claimed is:

1. A compound of formula (I) which is 4-(8-methoxy-1-(1-methoxypropan-2-yl)-2-(tetrahydro-2H-pyran-4-yl)-1H-imidazo[4,5-c]quinolin-7-yl)-3,5-dimethylisoxazole

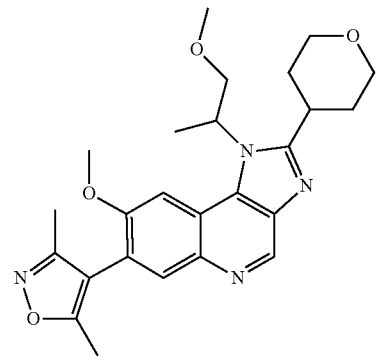 [SMILES: COCC(C)n1c(C2CCOCC2)nc2cnc3cc(-c4c(C)noc4C)c(OC)cc3c21]

(I)

or a salt thereof.

2. A compound of formula (IA) which is 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole

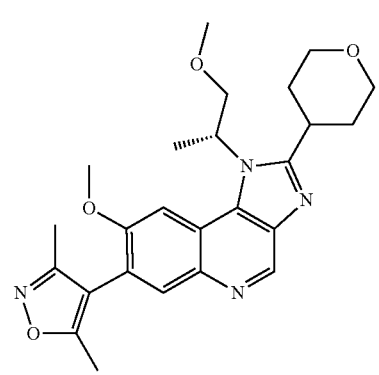

(IA)

or a salt thereof.

3. A compound of formula (IB) which is 4-(8-methoxy-1-((S)-1-methoxypropan-2-yl)-2-(tetrahydro-2H-pyran-4-yl)-1H-imidazo[4,5-c]quinolin-7-yl)-3,5-dimethylisoxazole

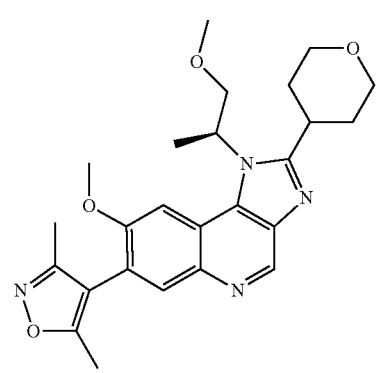 [SMILES: COC[C@H](C)n1c(C2CCOCC2)nc2cnc3cc(-c4c(C)noc4C)c(OC)cc3c21]

(IB)

or a salt thereof.

4. A compound according to claim 2 or a pharmaceutically acceptable salt thereof.

5. A pharmaceutical composition which comprises a compound or a pharmaceutically acceptable salt thereof as defined in claim 4 and one or more pharmaceutically acceptable carriers, diluents or excipients.

6. A combination pharmaceutical product comprising a compound or a pharmaceutically acceptable salt thereof as defined in claim 4 together with one or more other therapeutically active agents.

7. A method of treating a chronic autoimmune and/or inflammatory condition which comprises administering, to a human subject in need thereof, a therapeutically effective amount of a compound or a pharmaceutically acceptable salt thereof as defined in claim 4.

8. A method of treating cancer which comprises administering, to a human subject in need thereof, a therapeutically effective amount of a compound or a pharmaceutically acceptable salt thereof as defined in claim 4.

9. A method according to claim 8 wherein said cancer is a leukaemia, a NUT-midline carcinoma, multiple myeloma, lung cancer, a neuroblastoma, Burkitt's lymphoma, cervical cancer, esophageal cancer, ovarian cancer, breast cancer, or colorectal cancer.

10. A salt of a compound of Formula (IA) according to claim 2 wherein said salt is selected from the group consisting of hydrochloride, sulfate, maleate, fumarate, citrate, p-toluenesulfonate, benzenesulfonate, and methanesulfonate salt.

11. A salt according to claim 10 wherein said salt is a methanesulfonate salt.

12. A compound of formula (IA) which is 4-(8-methoxy-1-((R)-1-methoxypropan-2-yl)-2-(tetrahydro-2H-pyran-4-yl)-1H-imidazo[4,5-c]quinolin-7-yl)-3,5-dimethylisoxazole.

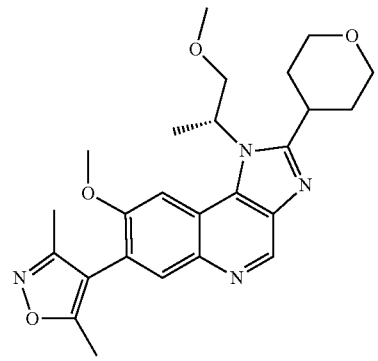

(IA)